United States Patent [19]
Miesel

[11] Patent Number: 5,919,221
[45] Date of Patent: *Jul. 6, 1999

[54] METHOD AND APPARATUS FOR CALIBRATING PACEMAKER PRESSURE SENSOR LEAD PRIOR TO CHRONIC IMPLANT

[75] Inventor: Keith A. Miesel, St. Paul, Minn.

[73] Assignee: Medtronic, Inc, Minneapolis, Minn.

[ * ] Notice: This patent issued on a continued prosecution application filed under 37 CFR 1.53(d), and is subject to the twenty year patent term provisions of 35 U.S.C. 154(a)(2).

[21] Appl. No.: 08/837,674

[22] Filed: Apr. 22, 1997

[51] Int. Cl.⁶ ........................................................ A61N 1/04
[52] U.S. Cl. .............................. 607/119; 73/1.63; 73/1.57
[58] Field of Search ...................... 73/1.57–1.63, 73/1.66–1.71; 607/27, 119, 122, 23; 600/488

[56] References Cited

U.S. PATENT DOCUMENTS

| | | |
|---|---|---|
| 4,052,991 | 10/1977 | Zacouto . |
| 4,182,158 | 1/1980 | Culotta et al. ............................ 73/1.58 |
| 4,384,470 | 5/1983 | Fiore ........................................ 73/1.68 |
| 4,901,735 | 2/1990 | Von Berg ................................. 73/1.62 |

FOREIGN PATENT DOCUMENTS 0 017 528  10/1980  European Pat. Off. .......... G02F 1/01

*Primary Examiner*—William E. Kamm
*Assistant Examiner*—George R. Evanisko
*Attorney, Agent, or Firm*—Harold R. Patton; Michael B. Atlass

[57] ABSTRACT

The present invention provides apparatus, systems, and methods for accurately calibrating a pressure sensor which is incorporated into a lead, e.g., a pacemaker lead, prior to implant into a patient. A calibration vessel is provided which has a housing which forms a reservoir for containing the portion of the lead having the pressure sensor. The vessel also has a connector for receiving a reference pressure into the reservoir, and a sealable opening for receiving the distal end of the lead that carries the pressure sensor. The calibration vessel can be used in a system comprising an electronic display module and an external pressure reference, for establishing an accurate sensor baseline for zero pressure; and can also be used in a system comprising an electronic display module, a reference pressure input source, and a manometer for establishing an accurate scale factor for the lead pressure sensor.

13 Claims, 6 Drawing Sheets

METHOD AND APPARATUS FOR CALIBRATING PACEMAKER PRESSURE SENSOR LEAD PRIOR TO CHRONIC IMPLANT

FIELD OF THE INVENTION

The present invention relates to apparatus, systems and methods for calibrating pressure sensor leads for pacemakers and other implantable medical devices prior to their implant in a patient.

BACKGROUND OF THE INVENTION

Leads or catheters having pressure sensors are used in a number of different implantable medical devices. For example, the Implantable Hemodynamic Monitor (IHM) made by Medtronic, Inc., assignee of this invention, continuously monitors right ventricular pressure. Pacemaker systems likewise employ pressure sensors and a number of other applications currently use pressure, or potentially can use pressure sensors for obtaining significant information.

Pacemaker leads having a pressure sensor are used in connection with cardiac pacemakers, and particularly in rate response pacemakers, e.g., VVIR, DDDR, etc. Pressure sensors may likewise be utilized on pacing leads for other purposes, such as determining capture by a delivered pace pulse. The pressure sensor on the pacemaker lead detects the pressure inside the heart chamber into which the lead is inserted, and converts the detected pressure into electronic information which is transmitted back to the pacemaker. The pacemaker then analyzes the information received from the pressure sensor and determines an appropriate rate response or uses the information for another purpose. Pacemaker systems utilizing, e.g., ventricular pressure, for determining an appropriate rate response are well known in the art. See U.S. Pat. Nos. 4,052,991 and 4,600,017; EPO Pub. No. 0 017 528.

Prior to implanting a pacemaker lead having a pressure sensor into a patient, it is critical to establish the accuracy of the pressure sensor. The accuracy of the pressure sensor can be divided into two parameters, "baseline pressure" and "scale factor." In regard to the former parameter, the pressure detected by the sensor must accurately reflect the true pressure inside the particular chamber into which it is inserted. Thus, the "baseline pressure" value of the sensor must be established relative to a known applied pressure. In regard to the latter parameter, any increase or decrease in pressure reported by the sensor in the chamber of the heart into which it has been inserted must accurately reflect the amount of pressure actually increased or decreased. Thus, an accurate "scale factor" for the sensor must be established, in order to have complete calibration. In addition, it is preferable that such parameters be adjusted within a sterile environment.

The accuracy of the pressure sensor is not guaranteed, or at least should not be relied upon by physicians, simply upon the manufacturer's packaging of the pacemaker lead. Once implanted into a patient, the pressure sensor accuracy cannot be easily verified. It has long been desired to provide reliable calibration of baseline and scale factor for a pressure sensor in a pacemaker lead, and to do so in a sterile environment. To this end, Applicant's invention is directed to apparatus and methods of using the apparatus to establish an accurate baseline and scale factor for a pressure sensor in a pacemaker lead in a sterile environment. In patients with cardiac conditions which require implantation of such a pacemaker lead, Applicant's invention provides easy but reliable calibration, to insure that accurate data is detected and transmitted to the pacemaker. Applicant's invention also provides the physician with confidence that sufficient care has been taken to accurately calibrate the pressure sensor of the pacemaker lead in a sterile environment. The use of the invention thus minimizes any need to replace or reprogram the implanted pacemaker to account for an inaccurate pressure sensor, much to the benefit of the patient.

Although the description of this invention uses an implantable pacemaker system as exemplary, it is to be noted that it applies equally to other uses and applications. In addition to the IHM described above, it is applicable to any system where pressure is sensed, e.g., for detecting tachycardia or fibrillation, detecting heart failure, etc.

SUMMARY OF THE INVENTION

In accordance with the above, the primary purpose of Applicants' claimed invention is to provide apparatus, systems, and methods for establishing an accurate baseline and scale factor for a pressure sensor in an implantable medical device system, prior implant in a patient. In a preferred embodiment, the invention is applicable to sensors in leads and catheters of pacemaker and monitoring systems. In another embodiment, it is applicable to calibrate sensors built into implantable devices such as pacemakers.

For a pacemaker application, once a patient has been diagnosed with a cardiac condition suggesting implantation of a pacemaker lead having a pressure sensor, the pressure sensor is calibrated by establishing an accurate baseline pressure and scale factor. Both calibrations, baseline pressure and scale factor, are performed in a sterile environment.

The primary element of the preferred embodiment of this invention is the calibration vessel. The vessel has a housing forming a vessel reservoir, which contains the portion of the pacemaker lead having the pressure sensor. The proximal end of the calibration vessel, the end through which the pacemaker lead is inserted, comprises a seal which provides an airtight seal between the vessel housing and the pacemaker lead. The distal end of the calibration vessel comprises a connector which connects the calibration vessel to either the atmosphere, or a input pressure source which functions in connection with a manometer.

The calibration system further comprises an electronic display module which is electrically connected to the pacemaker lead, for determining and displaying the pressure sensor output. In addition, an external pressure reference is electrically connected to the electronics display module.

The present invention also provides a method of establishing an accurate baseline pressure for a pacemaker lead having a pressure sensor. A calibration vessel, such as one described above, is provided, and the distal end of the pacemaker lead having the pressure sensor is inserted through the seal in the proximal end of the calibration vessel and into the vessel reservoir. The proximal end of the pacemaker lead, which is outside of the calibration vessel, is electrically connected to an electronic display module. The electronic display module is further electrically connected to an external pressure reference. The connector of the distal end of the vessel housing is opened to the atmosphere. The pressure detected by the pressure sensor on the pacemaker lead in the calibration vessel is algebraically subtracted with respect to the pressure detected by the external pressure reference; if the pressures do not zero out, the pressure sensor on the pacemaker lead is adjusted until the pressures are algebraically subtractive to zero, thereby calibrating the baseline.

The present invention also provides calibration systems used in establishing an accurate scale factor in a sterile environment for a pacemaker lead containing a pressure sensor. The calibration system comprises a calibration vessel, such as, for example, the calibration vessel described above. An electronic display module is also provided and is electrically connected to the pacemaker lead. In addition, a variable pressure input source with a manometer is provided and connected to the calibration vessel for calibrating the sensor response at different pressure levels.

The present invention also provides a method of establishing an accurate scale factor for a pacemaker lead containing a pressure sensor. A calibration vessel, such as one described above, is provided and the distal end of the pacemaker lead having the pressure sensor is inserted through the seal in the proximal end of the calibration vessel and into the vessel reservoir. The proximal end of the pacemaker lead, which is not inside the calibration vessel, is electrically connected to an electronic display module. A pressure input device is connected to the connector on the distal end of the vessel housing. Again pressure is exerted from the pressure input source into the vessel reservoir, and compared to the pressure detected by the pressure sensor on the pacemaker lead in the calibration vessel. If the source pressure as indicated on the manometer does not match the pressure sensor output, the lead sensor is adjusted until the amounts of the pressures are identical.

In another embodiment, the pressure sensor is calibrated while the lead is connected to the monitoring device, e.g., pacemaker, monitor, etc. and the device is in telemetric communication with an external programmer.

DESCRIPTION OF THE PREFERRED EMBODIMENTS

Applicant's invention provides apparatus, systems, and methods for establishing an accurate baseline pressure and scale factor for a lead having a pressure sensor, the lead being part of an implantable medical device system. The following discussion of FIGS. 1–5 relates to a pacemaker application but, as has been noted, the invention is also applicable to other systems.

Figure 1:
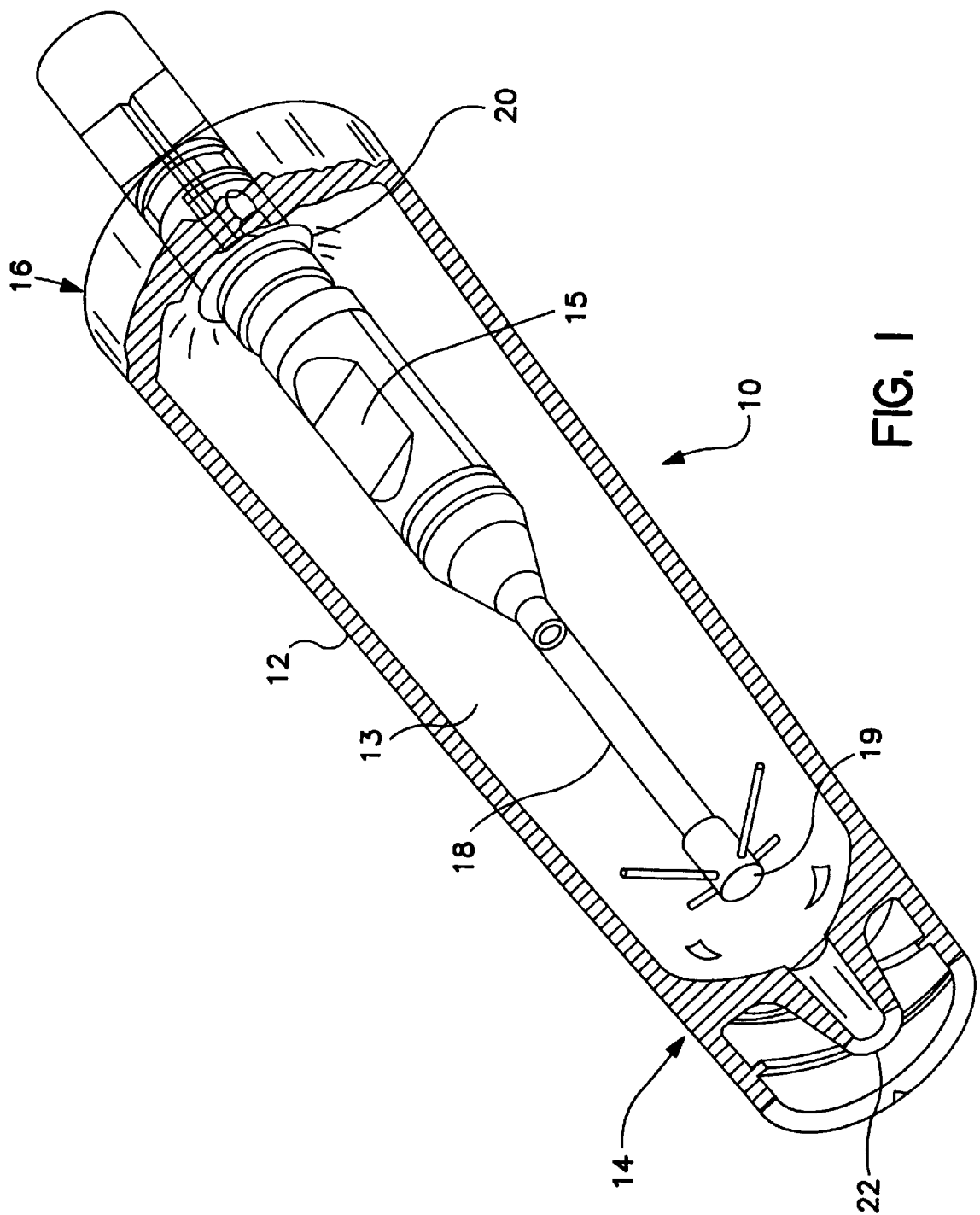
FIG. 1 illustrates a preferred embodiment of the calibration vessel of the present invention used in establishing an accurate baseline and scale factor of a pacemaker lead having a pressure sensor.

Referring now to FIG. 1, a preferred embodiment of a calibration vessel of the present invention is shown. As illustrated, the calibration vessel 10 comprises a vessel housing 12, which forms an interior vessel reservoir 13. In preferred embodiments of the invention, the vessel housing 12 is a tube or cylinder into which the distal portion of pacemaker lead 18 is inserted. It is to be understood, however, that other forms of the vessel housing 12 are within the scope of the present invention. Additional vessel housing embodiments include, for example, spherical bodies and the like. In preferred embodiments of the invention, the vessel housing 12 is made of materials that are easily removed from the pacemaker lead 18, i.e., can be easily peeled away from the pacemaker lead 18 and disposed of after performing the methods of the invention. Materials such as plastics and the like can be used for making the vessel housing 12.

Still referring to FIG. 1, the vessel housing 12 comprises a proximal end 16. The proximal end 16 is the end through which the portion of the pacemaker lead 18 having the pressure sensor 15 is inserted into the vessel reservoir 13. Conductors (not shown) are connected to the pressure sensor 15 and lead back to the proximal end of the pacemaker lead 18, where they are connected to a pacemaker (not shown). A seal 20, located at the proximal end 16, provides an airtight seal between the pacemaker lead 18 and the reservoir 13, such that no air can move into or out of the reservoir 13 through proximal end 16. In preferred embodiments of the present invention, the seal 20 is a rubber seal through which the pacemaker lead 18 is inserted. Alternately, the seal 20 is a rubber gasket, o-ring, or the like. In other embodiments of the present invention, a sealing lubricant can be used in conjunction with the seal 20 in order to provide for a better air tight seal.

Still referring to FIG. 1, the vessel housing 12 also comprises a distal end 14. As illustrated, the lead has been inserted into vessel 10 so that the distal end of the pacemaker lead 18, carrying electrode 19, is in the proximity of connector 22 positioned axially in distal end 14. In preferred embodiments of the present invention, the connector 22 is a leur-lock connector. It is to be understood, however, that other forms of connector 22 are within the scope of the present invention. The connector 22 provides for the connection between the vessel housing 12 and a pressure input source 30 (shown in FIG. 4).

In preferred embodiments of the present invention, the calibration vessel 10 is compression cast around the pacemaker lead 18 following manufacture of the lead. In this embodiment, the calibration vessel 10 is pre-packaged by the manufacturer along with the pacemaker lead 18. The package is then sterilized in an appropriate manner, i.e. by chemical or by pressure-temperature means. Alternately, the physician or technician opens the packaged pacemaker lead 18 in a sterile environment, such as a sterile hood, or by other such means; the pacemaker lead 18, which has been appropriately sterilized, is then inserted through the seal 20 at the proximal end 16 of calibration vessel 10, into the vessel reservoir 13 by the physician or technician who uses the pacemaker lead 18.

Figure 2:
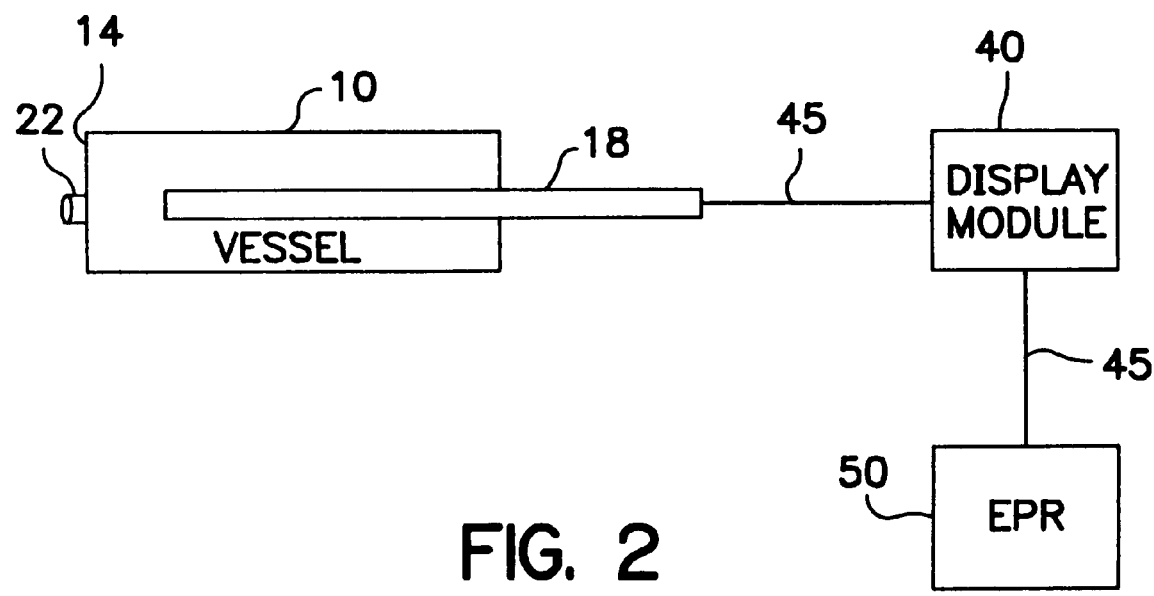
FIG. 2 is a schematic representation of a calibration system in accordance with the present invention, illustrating the elements used to establish an accurate baseline pressure for a pacemaker lead having a pressure sensor.

Referring now to FIG. 2, illustrated is a schematic representation of a calibration system used in establishing an accurate baseline pressure in a sterile environment for a pacemaker lead containing a pressure sensor, in accordance with the present invention. The calibration system comprises a calibration vessel 10, such as one described above, into which the distal portion of lead 18 has been inserted so that sensor 15 is sealed within reservoir 13. An electronic display module 40 is electrically connected to the proximal end of the pacemaker lead 18. In addition, the calibration system also includes an external pressure reference 50, which measures ambient barometric pressure and provides an electrical baseline reference signal which is electrically connected to electronic display module 40. The electrical connection between the proximal end of the pacemaker lead 18 and the electronic display module 40, as well as between the electronic display module 40 and the external pressure reference 50, can be made by using typical electrical cables 45. Electronic display modules 40 are well known to the skilled artisan. In some embodiments of the invention, the electronic display module 40 can be a cardiac monitor which receives the two inputs. The external pressure reference 50, which provides an outside source by which to measure external barometric pressure, is well known to those skilled in the art. Preferably, the external pressure reference 50 is standardized and/or certified for its accuracy. In the calibration system for establishing an accurate pressure baseline, the distal end 14 of the vessel housing 12 of the calibration vessel 10 is open to the atmosphere. That is, the connector 22 of the distal end 14 of the vessel housing 12 is open.

In the above-referenced Implantable Hemodynamic Monitor (IHM) system, an electronic display module is part of a PC-based programmer. The IHM system continually monitors right ventricular pressure. In order to subtract atmospheric pressure to arrive at a gauge pressure, the patient carries a recording barometer which logs atmospheric data for later time-synchronization with right ventricular pressure. Thus, the recorded atmospheric pressure is subtracted from the monitored right ventricular pressure to provide the differential pressure which is to be used for diagnosis. In this system, this external barometer is used as the external reference for the purpose of zeroing the lead-based sensor. It is to be noted that in this case, the atmospheric reference need not even be accurate with respect to actual atmospheric pressure, since it is the differential pressure, i.e., the difference between the sensor and the external reference sensor, which is used for diagnosis. It is important that the two pressures agree when the same pressure is applied to each, that changes in pressure are recorded accurately, and that the baseline pressure measurement is stable over time.

Figure 3:
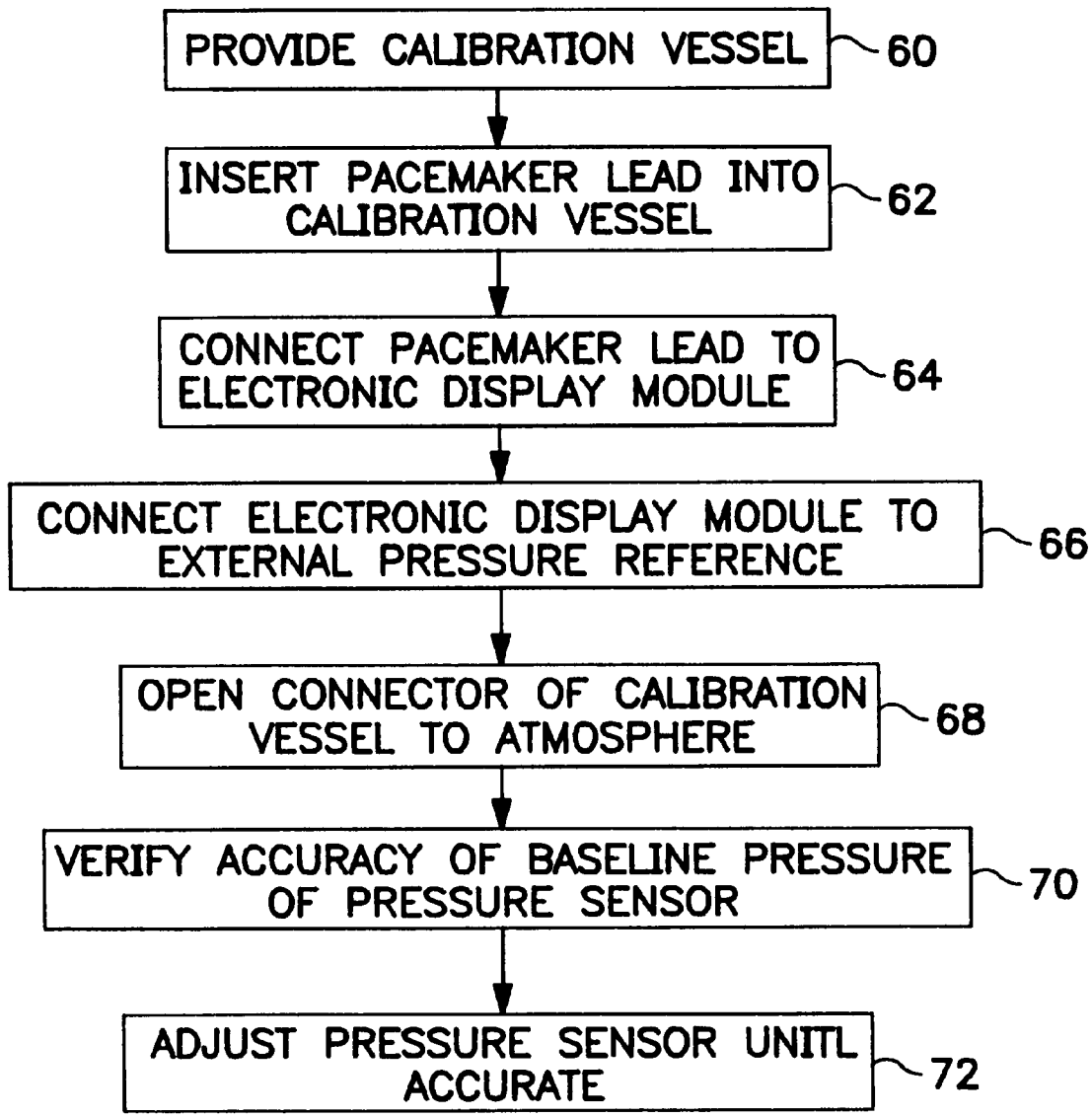
FIG. 3 is a flow diagram showing the steps of a method of calibrating baseline pressure for a pacemaker lead having a pressure sensor, in accordance with the present invention.

Referring now to FIG. 3, there is shown a flow diagram illustrating the steps involved in a method of establishing an accurate baseline pressure for a pacemaker lead pressure sensor, in accordance with the present invention. The first step 60 is to provide a calibration vessel 10, such as, for example, the calibration vessel described above. The second step 62 is to insert the distal end of the pacemaker lead 18, which contains the pressure sensor 15, through the seal 20 of the proximal end 16 of the vessel housing 12 of the calibration vessel 10. Next, as illustrated at step 64, the electrical output from the proximal end of the pacemaker lead 18 is connected to a first input of electronic display module 40. Then, at step 66, the electronic output of external pressure reference 50 is connected. Next, as shown at 68, the distal end of the vessel housing 12 is connected to the atmosphere by opening the connector 22. Steps 60, 62, 64, 66, and 68 function to set up the calibration system illustrated in FIG. 2, and can be performed in any particular order. After this, as shown at step 70, the accuracy of the baseline pressure of the pressure sensor 15 is verified by comparing the pressure detected by the lead pressure sensor 15 in the calibration vessel 10 and the pressure detected by the external pressure reference 50. If the detected pressures are the same, the baseline pressure of the pressure sensor 15 is accurate. If not, the pressure sensor 15 is adjusted until the detected pressures are the same, as shown at 72.

At all times during this calibration procedure, the pacemaker lead 18 and the calibration vessel 10 are kept in a sterile environment. The physician or technician verifies that the pressure detected by the pressure sensor 15 is the same as the pressure detected by the external pressure reference 50 by using the electronics display module 40, which is connected to display the differential of the two input signals. If the detected pressures are the same, and therefore the pressure sensor is accurate, the value shown on the electronics display module 40 will be zero. That is, the input from the pressure sensor 15 and the input from the external pressure reference 50 will be algebraically subtractive. If the reading on the electronics display module 40 is not zero, the physician can adjust the pressure sensor 15 until the reading is zero by manipulating calibration coefficients of the pressure sensor 15. This can also be accomplished automatically by use of an algorithm in a PC-based module or program 40.

Figure 4:
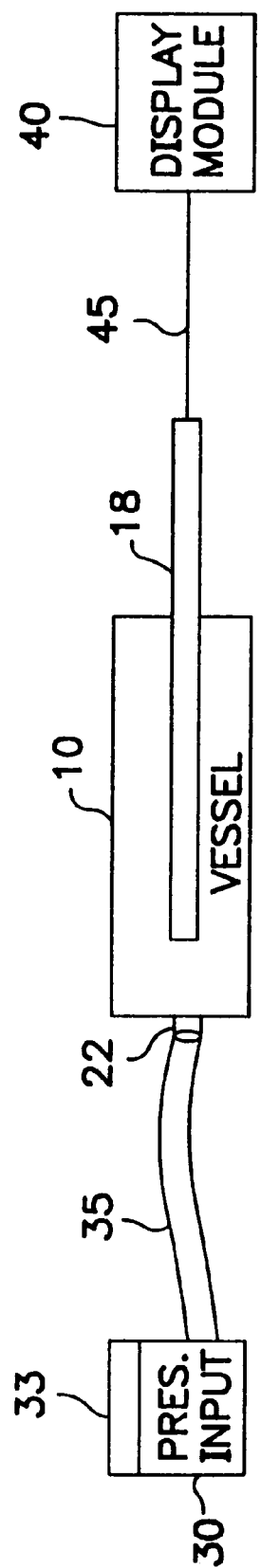
FIG. 4 is a schematic representation of a calibration system in accordance with the present invention, illustrating the elements used to establish an accurate scale factor for a pacemaker lead having a pressure sensor.

Referring now to FIG. 4, there is illustrated a schematic representation of a calibration system for establishing an accurate scale factor for a pacemaker lead pressure sensor, and for performing this calibration step in a sterile environment. The calibration system comprises a calibration vessel 10, such as one described above. An electronic display module 40 is electrically connected by cable 45 to receive the sensor signal from proximal end of the pacemaker lead 18 upon inserting the portion of the pacemaker lead 18 containing the pressure sensor 15 into the vessel reservoir 13. In addition, the calibration system also includes a pressure input source 30 connected by tubing 35 to vessel connector 22, to place the interior of the vessel under a prescribed pressure. A manometer 33, which may be part of the same apparatus or separate from the source, measures the amount of pressure exerted by the pressure input source 30. Preferred pressure input sources include, for example, a pump, squeeze-bulb, in-house air lines, and the like.

Figure 5:
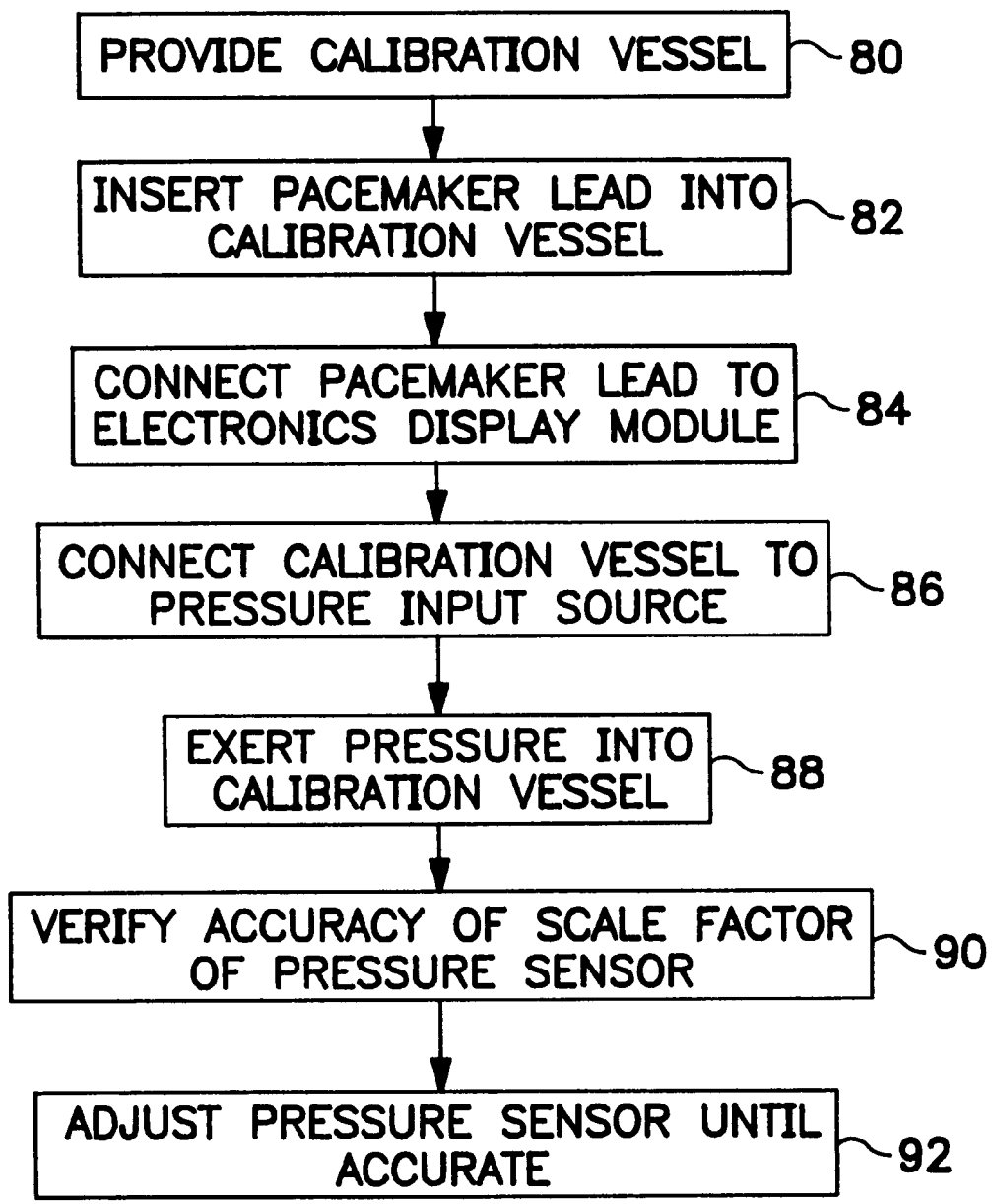
FIG. 5 is a flow diagram showing the steps of a method of establishing an accurate scale factor for a pacemaker lead having a pressure sensor, in accordance with the present invention.

Referring now to FIG. 5, shown is a flow diagram illustrating the steps involved establishing an accurate scale factor for a pacemaker lead pressure sensor, in accordance with the present invention. Note that the pacemaker contains stored data for use in processing the received pressure signals, which data includes the given scale factor for the sensor, i.e., the scale factor given by the sensor manufacturer. Thus, the actual scale factor of the sensor must be verified to be the same as the stored scale factor, or else the pressure signals would be erroneously translated.

The first step 80 is to provide a calibration vessel 10, such as, for example, the calibration vessel described above. Next, at step 82, the distal end of the lead 18, which contains the pressure sensor 15, is inserted through the seal 20 of the proximal end 16 of the vessel housing 12 into the vessel reservoir 13. These steps may be done during the manufacturing process, or at the time of calibration. The next step 84 comprises electrically connecting the proximal end of the pacemaker lead 18 to an electronic display module 40. At 86, the calibration vessel 10 is connected to the pressure input source 30. Steps 80, 82, 84, and 86 function to produce the calibration system illustrated in FIG. 4, and can be performed in any desired order. With the calibration system ready to go, the next step is providing a given pressure into the calibration vessel 10 from the pressure input source 30, as shown at 88. The pressure or pressures exerted can vary, and may range from the typical pressure changes normally detected inside a particular chamber of the heart. Next, at step 90, the accuracy of the scale factor is verified by comparing the source pressure as seen on the manometer, to the pressure detected by the pressure sensor 15. This step involves translating the voltage signal on monitor 40 by the sensor scale factor as stored in the pacemaker, to determine the sensor-indicated pressure. Thus, for a given manometer value, the electrical signal seen at the monitor should accord with the pacemaker scale factor. If the pressures are identical, the scale factor of the pressure sensor 15 is accurate. If not, as indicated at step 92, the pressure sensor 15 on the pacemaker lead 18 is adjusted until the detected pressures are identical. Steps 88, 90, and 92 can be performed numerous times with a range of known pressures exerted from the pressure input source 30 if desired. At all times during this calibration procedure, the pacemaker lead 18 and the calibration vessel 10 are kept in a sterile environment.

In the IHM embodiment, the primary objective is to verify proper functioning of the sensor prior to implant. If significant scale factor error is observed, the appropriate response may not be to attempt to calibrate, but to discard the lead in favor of one that checks out accurately. The calibration vessel of the present invention can also be used to calibrate sensors for sensing parameters other than pressure, depending upon the particular pacemaker lead used. For example, the accuracy of a pH detector on a pacemaker lead can be established by using the calibration vessel described above. The calibration systems and methods described above can be easily converted to an appropriate system for establishing an accurate baseline pH as well as an accurate scale factor for pH, by using, for example, a certified reference source for pH as well as various solutions of known pH. Likewise, the calibration systems and methods described above can be easily converted to calibrate oxygen for a particular pacemaker lead having an oxygen detector.

After any of the above-described calibration procedures are performed, the pacemaker lead 18 is removed from the calibration vessel 10. Preferably, the calibration vessel 10 is peeled away from the pacemaker lead 18, leaving the lead with calibrated sensor ready for direct implantation.

It should also be apparent that a vessel can be constructed to temporarily house a portion of or an entire implantable device if the pressure or other sensor being calibrated is on or in the implant's housing.

Figure 6:
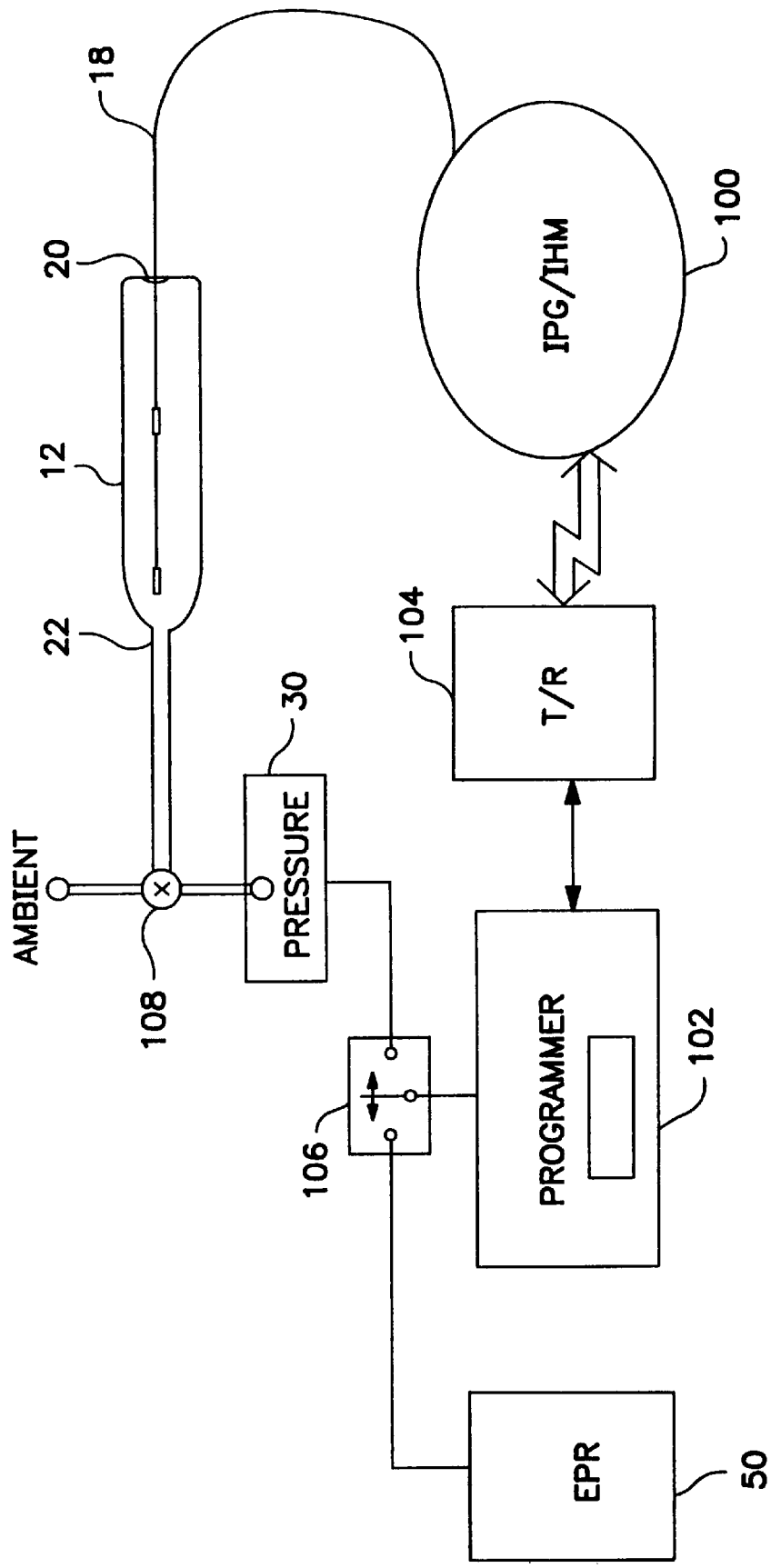
FIG. 6 is a schematic representation of a calibration system for calibrating a pressure sensor of an implantable system, under conditions where the implantable system is in telemetric communication with an external programmer.

Referring now to FIG. 6, there is shown a calibration system arrangement for calibrating an entire medical device system which functions as it is to function when the device and lead are implanted. As seen in FIG. 6, the device 100, either a pacemaker (PIG) or an IHM or like device, is connected to the proximal end of the lead 18. The distal end of the lead, carrying the pressure sensor, is inserted through seal 20 into the vessel 12, as described above. The implantable device, not yet implanted for the calibration test, is in communication with a programmer 102 through a telemetry transmit/receive (TR) device 104, in accordance with known technology. In this system, pressure readings taken by the lead when it is implanted in a patient, are transmitted to the external programmer 102, and likewise program instructions can be transmitted to the device 100.

The arrangement of FIG. 6 has the advantage of calibrating the sensor when the entire system is used, so that assurance is provided that the pressure data that is actually brought out to the programmer is accurate. When the baseline is being checked, the external pressure reference (EPR) 50 measures the ambient pressure, and connects a corresponding electrical signal through switch 106 to programmer 102. At the same time, the T-type air passage device 108 is switched to provide ambient pressure through connector 22 to the interior of vessel 12. The sensor reading is communicated through lead 18 to the device 100, which in turn downloads data through T/R 104 to the programmer 102. The programmer 102 compares the two readings, and determines whether the sensor carried by lead 18 is providing an accurate baseline. For scale factor measurements, the pressure source 30 is used, which provides an actual pressure switched through T-device 108 to the interior of the vessel 12, while a corresponding electrical output indicative of the pressure source is connected through switch 106 to the programmer 102, where the scale factor comparison is made.

It is to be noted that in some medical devices, the pressure transducer is located in the device 100, and pressure is transferred through a lumen in the lead 18 to the pressure transducer. This invention is likewise applicable to this arrangement. Further, for an implantable device having the pressure transducer mounted on its case, or just under the case where it can receive pressure variations, a vessel can be adapted with appropriate geometry to receive the device itself.

What is claimed is:

1. A calibration vessel adapted for use in a sterile environment, for baseline and scale factor calibration of a lead pressure sensor having a pressure sensor located on a distal end thereof, comprising:

a vessel having a proximal end, a distal end, and an interior reservoir for containing said lead distal end;

said proximal end of said vessel having sealable opening means for admitting said lead distal end into said reservoir while providing an airtight seal between said reservoir and the exterior of said vessel; and said distal end of said vessel having connecting means for providing a connection between said vessel reservoir and a pressure input source, and wherein said vessel further comprises a housing which is adapted and disposed to be affixed to said lead distal end and wherein said vessel housing comprises a peel-away material adapted to peel-away from said lead.

2. The vessel of claim 1 wherein said vessel comprises a tubular housing which forms said reservoir.

3. The vessel of claim 2, wherein said sealable opening means comprises a rubber seal, and said connecting means comprises a leur-lock interface.

4. The vessel of claim 1, and wherein said sealable opening means is sized to admit said lead distal end.

5. The combination of a pressure sensor calibration system and a lead, said lead having a sensor at about its distal end which provides an electrical output representative of a body parameter, and an electrical connection from said sensor output to the lead proximal end, said combination comprising:

said lead having a distal end comprising a pressure sensor and a proximal end, oppositely located from said distal end, a calibration vessel for containing said lead distal end, said vessel having a vessel housing with a proximal end and a distal end, said vessel housing forming a vessel reservoir for containing said lead distal end, said proximal end of said vessel housing having sealing means for providing an airtight seal between said vessel reservoir and said lead, and said distal end of said vessel housing having connecting means for providing a connection between said reservoir to a pressure external to said reservoir; and an electronic display module electrically connected to said lead proximal end to receive and display said sensor output and wherein said lead is a pacemaker lead, and said sensor is a pressure sensor.

6. The combination of a pressure sensor calibration system and a lead, said lead having a sensor at about its distal end which provides an electrical output representative of a body parameter, and an electrical connection from said sensor output to the lead proximal end, said combination comprising:

said lead having a distal end comprising a pressure sensor and a proximal en, oppositely located from said distal end, a calibration vessel for containing said lead distal end, said vessel having a vessel housing with a proximal end and a distal end, said vessel housing forming a vessel reservoir for containing said lead distal end, said proximal end of said vessel housing having sealing means for providing an airtight seal between said vessel reservoir and said lead, and said distal end of said vessel housing having connecting means for connecting said reservoir to a pressure external to said reservoir; and an electronic display module electrically connected to said lead proximal end to receive and display said sensor output, said system further comprising:

an external pressure reference which provides an electrical signal representative of atmospheric pressure, said atmospheric signal being electrically connected to said electronic display module; and said electronic display module providing an output indication of the difference between said sensor output and said atmospheric signal.

7. The combination as described in claim 6, further comprising an external pressure source connected to said connecting means.

8. The combination as described in claim 6, wherein said vessel housing is a tube, said sealing means is a rubber seal, and said connecting means is a leur-lock interface.

9. The combination of as described in claim 6, wherein said vessel housing comprises peel-away material adapted to peel-away from said pacemaker lead.

10. A method of establishing an accurate baseline for a pressure sensor incorporated into a lead for use with an implantable medical device, said lead having said sensor located at its distal end and an output from said sensor located at its proximal end, comprising:

providing a calibration vessel which has an interior reservoir for containing said distal end of said pacemaker lead, said vessel having a proximal end and a distal end;

inserting said lead distal end through said vessel proximal end so that said lead distal end is sealed within said reservoir at said vessel proximal end;

opening said vessel reservoir at said vessel distal end to atmospheric pressure;

providing a display means for displaying a differential of two electrical signals connected thereto;

connecting a first electrical signal representative of atmospheric pressure to said display means, to provide a first of said two electrical signals;

connecting said sensor output from said lead proximal end to said display means, to provide a second of said two electrical signals; and adjusting said sensor so that said display means displays a substantially zero differential.

11. A method of calibrating a pressure sensor incorporated into a pacemaker lead, said lead having said sensor located at its distal end and an output from said sensor at its proximal end, comprising:

providing a calibration vessel which has an interior reservoir for containing said distal end of said pacemaker lead, said vessel having a proximal end and a distal end;

inserting said lead distal end through said vessel proximal end so that said lead distal end is sealed within said reservoir at said vessel proximal end;

providing a known pressure to said vessel reservoir;

providing a display means for displaying an indication of a value represented in an electrical signal;

connecting said sensor output from said lead proximal end to said display means so as to supply an electrical signal representative of sensor output from said lead to said display means; and adjusting said sensor so that said display indication accurately corresponds to said known pressure.

12. A combination of a lead for connection to a medical device and a calibration vessel, comprising:

said lead having a distal end and a proximal end, said lead comprising at least one electrode positioned at about said lead distal end, a pressure sensor incorporated into said lead near said lead distal end, and connecting means for electrically connecting said sensor to a sensor output at said lead proximal end, and said electrode to an electrode terminal at said lead proximal end; and said calibration vessel being adhered to a distal portion of said lead, said vessel having a reservoir in which said sensor is enclosed, seal means for sealing said vessel around said lead at a location proximal to said sensor, and pressure communicating means for communicating a given pressure to reservoir.

13. The combination as described in claim 12, wherein said vessel comprises means for peeling said vessel away from said lead.

* * * * *